United States Patent [19]

Mickel et al.

[11] Patent Number: 5,332,729

[45] Date of Patent: Jul. 26, 1994

[54] N-ARALKYL- AND N-HETEROARALKYL-AMINOALKANE-PHOSPHINIC ACIDS

[75] Inventors: Stuart J. Mickel, Lausen; Wolfgang Fröstl, Basel, both of Switzerland; Pascal Furet, Thann, France

[73] Assignee: Ciba-Geigy Corporation, Ardsley, N.Y.

[21] Appl. No.: 56,082

[22] Filed: May 3, 1993

[30] Foreign Application Priority Data

May 8, 1992 [CH] Switzerland .......................... 1480/92

[51] Int. Cl.$^5$ ................. B01J 31/00; A61K 31/66; C07F 9/30; C07F 9/58
[52] U.S. Cl. .................... 514/114; 514/89; 562/11; 558/166; 546/89
[58] Field of Search ............. 562/11; 514/89, 114; 558/166; 546/89

[56] References Cited

U.S. PATENT DOCUMENTS

| D. 302,521 | 8/1989 | Grinde | D9/375 |
|---|---|---|---|
| 3,493,639 | 2/1970 | Tavs | 260/969 |
| 3,812,221 | 5/1974 | Braden et al. | 260/968 |
| 4,536,355 | 8/1985 | Lee et al. | 260/944 |
| 4,618,358 | 10/1986 | Maier | 71/86 |
| 4,656,298 | 4/1987 | Digwall et al. | 556/12 |
| 4,772,738 | 9/1988 | Dingwall et al. | 558/175 |
| 4,908,465 | 3/1990 | Dingwall et al. | 558/175 |
| 5,004,826 | 4/1991 | Dingwall et al. | 558/169 |
| 5,013,863 | 5/1991 | Baylis et al. | 562/11 |
| 5,051,524 | 9/1991 | Baylis et al. | 558/145 |
| 5,064,819 | 11/1991 | Baylis et al. | 514/114 |
| 5,190,933 | 3/1993 | Baylis et al. | 514/114 |
| 5,190,934 | 3/1993 | Mickel et al. | 514/114 |
| 5,212,164 | 5/1993 | Biller et al. | 562/11 |

FOREIGN PATENT DOCUMENTS

| 2045077 | 6/1991 | Canada | 562/11 |
|---|---|---|---|
| 0181833 | 5/1986 | European Pat. Off. | |
| 0319482 | 6/1989 | European Pat. Off. | |
| 0356128 | 2/1990 | European Pat. Off. | |
| 0463560 | 1/1992 | European Pat. Off. | 562/11 |
| 257078 | 4/1986 | France | 562/11 |
| 0014129 | 8/1972 | Japan | 562/11 |
| 0063024 | 5/1979 | Japan | 562/11 |
| 1525262 | 9/1978 | United Kingdom | |

OTHER PUBLICATIONS

Dingwall, J., "New Carboxyphosphonic and Phosphinic Acid Structures of Technical and Biological Interest", Phosphorous and Sulphur, vol. 18, pp. 353–356 (1983).

Annual Meeting of the American Academy of Neurology, Neurology, 41(Suppl. 1), p. 151, Mar. 1991, Abstracts 1 and 3.

Annual Meeting of the Society for Neuroscience, Nov. 10–15, (1991), vol. 17, 1991.

Chemical Abstracts, vol. 97, 72585v, (1982), Rupp et al., "Herbicidal Methylphosphinic Acid Derivatives".

Primary Examiner—José G. Dees
Assistant Examiner—Keith MacMillan
Attorney, Agent, or Firm—Karen G. Kaiser; Irving M. Fishman

[57] ABSTRACT

N-aralkyl- and N-heteroaralkyl-aminoalkanephosphinic acids of formula I $$\begin{array}{c} HO\diagdown\underset{\|}{O} \quad R_1 \quad\quad R_2 \\ \diagdown P-CH_2-CH-CH_2-N\diagup \\ R\diagup \quad\quad\quad\quad\quad\quad\quad\diagdown R_3 \end{array} \quad (I)$$

wherein

R is an aliphatic, cycloaliphatic, cycloaliphatic-aliphatic, araliphatic or heteroarylaliphatic radical having at least 2 carbon atoms, $R_1$ is hydrogen or hydroxy, $R_2$ is an araliphatic or heteroarylaliphatic radical substituted by free or functionally modified carboxy that is bonded directly or by way of a spacer, and $R_3$ is hydrogen, lower alkyl or a group $R_2$, and the salts thereof have valuable nootropic and anti-epileptic properties and can be used in the preparation of a nootropic or anti-epileptic medicament.

19 Claims, No Drawings

N-ARALKYL- AND N-HETEROARALKYL-AMINOALKANEPHOSPHINIC ACIDS

The invention relates to novel N-aralkyl- and N-heteroaralkyl-aminoalkanephosphinic acids of formula I

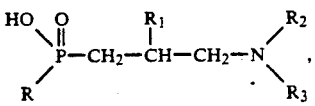

wherein

R is an aliphatic, cycloaliphatic, cycloaliphatic-aliphatic, araliphatic or heteroarylaliphatic radical having at least 2 carbon atoms, $R_1$ is hydrogen or hydroxy, $R_2$ is an araliphatic or heteroarylaliphatic radical substituted by free or functionally modified carboxy that is bonded directly or by way of a spacer, and $R_3$ is hydrogen, lower alkyl or a group $R_2$, and to the salts thereof, to processes for the preparation thereof, to pharmaceutical compositions comprising them and to their use as the active ingredients of medicaments.

Aliphatic radicals R are, for example, lower alkyl having at least 2 carbon atoms, lower alkenyl, lower alkynyl, oxo-lower alkyl, hydroxy- or dihydroxy-lower alkyl, hydroxy-lower alkenyl, mono-, di- or poly-halo-lower alkyl, mono-, di- or poly-halo-lower alkenyl, mono-, di- or poly-halo(hydroxy)-lower alkyl, mono-, di- or poly-halo(hydroxy)-lower alkenyl, lower alkoxy-lower alkyl, di-lower alkoxy-lower alkyl, lower alkoxy(hydroxy)-lower alkyl, lower alkoxy(halo)-lower alkyl, lower alkylthio-lower alkyl and di-lower alkylthio-lower alkyl.

Cycloaliphatic radicals R are, for example, cycloalkyl, hydroxycycloalkyl, oxa-, dioxa-, thia- and dithia-cycloalkyl.

Cycloaliphatic-aliphatic radicals R are, for example, cycloalkyl-lower alkyl, cyclo-alkenyl-lower alkyl, cycloalkyl(hydroxy)-lower alkyl and (lower alkylthio)cycloalkyl(hydroxy)-lower alkyl.

Araliphatic radicals R are, for example, phenyl-lower alkyl radicals that are unsubstituted or mono-, di- or tri-substituted by lower alkyl, lower alkoxy, hydroxy, halogen and/or by trifluoromethyl, preferably α-phenyl-lower alkyl substituted as indicated or unsubstituted α,α-diphenyl- or α-naphthyl-lower alkyl.

Heteroarylaliphatic radicals R are, for example, thienyl-, furyl- or pyridyl-lower alkyl radicals that are unsubstituted or substituted, especially mono- or di-substituted, by halogen, preferably unsubstituted α-thienyl-, α-furyl- or α-pyridyl-lower alkyl.

Araliphatic or heteroarylaliphatic radicals $R_2$ substituted by free or functionally modified carboxy that is bonded directly or by way of a spacer are, for example, phenyl-, thienyl-, furyl- or pyridyl-lower alkyl radicals that are mono- or di-substituted by carboxy, esterified carboxy, amidated carboxy, cyano or by carboxy or cyano incorporated into a heteroaromatic ring system, each of which substituents is bonded directly or by way of a spacer, and which phenyl-, thienyl-, furyl- or pyridyl-lower alkyl radicals may be additionally substituted by a further electronegative group. In this context, a spacer is to be understood, for example, as a lower alkyl(id)ene group; esterified carboxy is to be understood, for example, as lower alkoxycarbonyl; amidated carboxy is to be understood, for example, as carbamoyl or N-mono- or N,N-di-lower alkylcarbamoyl; carboxy or cyano incorporated into a heteroaromatic ring system is to be understood, for example, as a five-membered azaoxa-, diazaoxa-, triaza- or tetraazaheteroaryl radical; and an electronegative group is to be understood, for example, as lower alkoxy, polyfluoro-lower alkoxy, halogen or polyfluoro-lower alkyl.

Suitable five-membered azaoxa-, diazaoxa-, triaza- or tetraazaheteroaryl radicals are, for example, the following, each of which is unsubstituted or substituted by lower alkyl, lower alkoxy, lower alkoxycarbonyl, cyano, hydroxy, amino or by halogen: oxazolyl, for example 5-$R_a$-oxazol-2-yl, isoxazolyl, for example 3-$R_a$-isoxazol-5-yl, oxadiazolyl, for example 3-$R_a$-1,2,4-oxadiazol-5-yl, 5-$R_a$-1,2,4-oxadiazol-3-yl or 5-$R_a$-1,3,4-oxadiazol-3-yl, triazolyl, for example 5-$R_a$-1,2,4-triazol-3-yl or 3-$R_a$-1,2,4-triazol-5-yl, or tetrazolyl, for example tetrazol-5-yl, $R_a$ being hydrogen or, in the second place, lower alkyl, lower alkoxy, lower alkoxycarbonyl, hydroxy, amino or halogen, and 1,2,4-oxadiazol-5-yl that is unsubstituted or substituted in the 3-position by amino or by halogen, such as chlorine, being preferred.

Hereinbefore and hereinafter, lower radicals and compounds are to be understood, for example, as those containing up to and including 7, preferably up to and including 4, carbon atoms.

Lower alkyl R is, for example, $C_2$–$C_7$alkyl, preferably $C_3$–$C_5$alkyl, such as propyl, isopropyl, butyl, isobutyl, sec-butyl, tert-butyl or pentyl, but may also be a $C_6$–$C_7$alkyl group, such as a hexyl or heptyl group.

Lower alkyl $R_3$ is, for example, $C_1$–$C_7$alkyl, preferably $C_1$–$C_4$alkyl, such as methyl, ethyl, propyl, isopropyl or butyl, but may also be isobutyl, sec-butyl, tert-butyl or a $C_5$–$C_7$alkyl group, such as a pentyl, hexyl or heptyl group.

Lower alkyl(id)ene is, for example, $C_1$–$C_4$alkylene, such as methylene, ethylene, 1,3-propylene or 1,4-butylene, or $C_2$–$C_4$alkylidene, such as ethylidene or isopropylidene.

Lower alkenyl is, for example, $C_2$–$C_4$alkenyl, such as vinyl, allyl or but-2-enyl, but may also be a $C_5$–$C_7$alkenyl group, such as a pentenyl, hexenyl or heptenyl group.

Lower alkynyl is, for example, $C_2$–$C_7$alkynyl, preferably $C_3$–$C_5$alkynyl, that carries the double bond in a position higher than the α,β-position, for example 2-propynyl (propargyl), but-3-yn-1-yl, but-2-yn-1-yl or pent-3-yn-1-yl.

Oxo-lower alkyl carries the oxo group preferably in a position higher than the α-position and is, for example, oxo-$C_2$–$C_7$alkyl, especially oxo-$C_3$–$C_6$alkyl, such as 2-oxopropyl, 2- or 3-oxobutyl or 3-oxopentyl.

Phenyl-lower alkyl is, for example, benzyl, 1-phenylethyl, 2-phenylprop-2-yl or, in the second place, 2-phenylethyl, 2-phenylprop-1-yl or 3-phenylprop-1-yl.

Thienyl-, furyl- or pyridyl-lower alkyl is, for example, thienyl-, furyl- or pyridyl-methyl, 1-thienyl-, 1-furyl- or 1-pyridyl-ethyl, 2-thienyl-, 2-furyl- or 2-pyridyl-prop-2-yl, or, in the second place, 2-thienyl-, 2-furyl- or 2-pyridyl-ethyl, 2-thienyl-, 2-furyl- or 2-pyridyl-prop-1-yl or 3-thienyl-, 3-furyl- or 3-pyridyl-prop-1-yl.

Hydroxy-lower alkyl carries the hydroxy group preferably in the α- or β-position and is, for example, corresponding hydroxy-$C_2$–$C_7$alkyl, such as 1-hydroxyethyl, 1- or 2-hydroxypropyl, 2-hydroxyprop-2-yl, 1- or 2-hydroxybutyl, 1-hydroxyisobutyl or 2-hydroxy-3-methylbutyl.

Dihydroxy-lower alkyl carries the hydroxy groups especially in the α,β-position and is, for example, α,β-dihydroxy-$C_3$–$C_7$alkyl, such as 1,2-dihydroxyprop-2-yl.

Hydroxy-lower alkenyl carries the hydroxy groups preferably in the α-position and the double bond preferably in a position higher than the α,β-position and is, for example, corresponding α-hydroxy-$C_3$–$C_5$alkenyl, for example 1-hydroxybut-2-enyl.

Mono-, di- or poly-halo-lower alkenyl is, for example, mono- di- or tri-fluoro-$C_2$–$C_5$alkenyl, such as 1-fluorobut-2-enyl.

Mono-, di- or tri-halo(hydroxy)-lower alkyl carries the hydroxy group preferably in the α-position and the halogen atoms preferably in a position higher than the α-position and is, for example, corresponding mono- di- or tri-fluoro-α-hydroxy-$C_2$–$C_7$alkyl, such as 4,4,4-trifluoro-1-hydroxybutyl.

Mono-, di- or poly-halo-lower alkyl is, for example, mono- di- or tri-fluoro-$C_2$–$C_5$alkyl, such as 3,3,3-trifluoropropyl, 4,4,4-trifluorobutyl, 1- or 2-fluorobutyl or 1,1-difluorobutyl.

Lower alkoxy is, for example, $C_1$–$C_7$alkoxy, preferably $C_1$–$C_4$alkoxy, such as methoxy, ethoxy, propoxy, isopropoxy or butoxy, but may also be isobutoxy, sec-butoxy, tert-butoxy or a $C_5$–$C_7$alkoxy group, such as a pentyloxy, hexyloxy or heptyloxy group.

Lower alkoxycarbonyl is, for example, $C_1$–$C_7$alkoxycarbonyl, preferably $C_1$–$C_4$alkoxycarbonyl, such as methoxy-, ethoxy-, propoxy-, isopropoxy- or butoxy-carbonyl, but may also be isobutoxycarbonyl, sec-butoxycarbonyl, tert-butoxycarbonyl or a $C_5$–$C_7$alkoxycarbonyl group, such as a pentyloxy-, hexyloxy- or heptyloxy-carbonyl group.

N-mono- or N,N-di-lower alkylcarbamoyl is, for example, N-mono- or N,N-di-$C_1$–$C_4$alkylcarbamoyl, such as methyl-, ethyl-, dimethyl- or diethyl-carbamoyl.

Carboxy-lower alkyl is, for example, carboxy-$C_1$–$C_4$alkyl, such as carboxymethyl.

Lower alkoxycarbonyl-lower alkyl is, for example, $C_1$–$C_4$alkoxycarbonyl-$C_1$–$C_4$alkyl, such as methoxy- or ethoxy-carbonylmethyl.

Cyano-lower alkyl is, for example, cyano-$C_1$–$C_4$alkyl, such as cyanomethyl.

Carbamoyl- or N-mono- or N,N-di-lower alkylcarbamoyl-lower alkyl is, for example, carbamoyl-$C_1$–$C_4$alkyl, such as carbamoylmethyl, or N-mono- or N,N-di-$C_1$–$C_4$alkylcarbamoyl-$C_1$–$C_4$alkyl, such as methyl-, ethyl-, dimethyl- or diethyl-carbamoylmethyl.

Polyfluoro-lower alkoxy is, for example, trifluoro-$C_1$–$C_4$alkoxy, such as trifluoromethoxy.

Polyfluoro-lower alkyl is, for example, trifluoro-$C_1$–$C_4$alkyl, such as trifluoromethyl or pentafluoroethyl.

Mono-, di- or tri-halo(hydroxy)-lower alkenyl carries the hydroxy group preferably in the α-position and the halogen atoms preferably in a position higher than the α-position and is, for example, corresponding mono-, di- or tri-fluoro-α-hydroxy-$C_2$–$C_5$alkenyl, such as 2-fluoro-1-hydroxybuten-2-yl.

Lower alkoxy-lower alkyl is, for example, $C_1$–$C_4$alkoxy-$C_1$–$C_4$alkyl, such as methoxy- or ethoxy-methyl, 2-methoxyethyl, 2-ethoxyethyl, 3-methoxy- or 3-ethoxy-propyl or 1- or 2-methoxybutyl.

Di-lower alkoxy-lower alkyl is, for example, di-$C_1$–$C_4$-alkoxy-$C_1$–$C_4$alkyl, for example dimethoxymethyl, dipropoxymethyl, 1,1- or 2,2-diethoxyethyl, diisopropoxymethyl, dibutoxymethyl or 3,3-dimethoxypropyl.

Lower alkoxy(hydroxy)-lower alkyl is, for example, $C_1$–$C_4$alkoxy-$C_2$–$C_7$-(hydroxy)alkyl, such as 2-hydroxy-3-methoxyprop-2-yl.

Lower alkoxy(halo)-lower alkyl is, for example, $C_1$–$C_4$alkoxy-$C_2$–$C_5$-(halo)alkyl, such as 2-fluoro-3-methoxybutyl.

Lower alkylthio-lower alkyl is, for example, $C_1$–$C_4$alkylthio-$C_1$–$C_4$alkyl, such as methylthio-or ethylthio-methyl, 2-methylthioethyl, 2-ethylthioethyl, 3-methylthio- or 3-ethylthio-propyl or 1- or 2-methylthiobutyl.

Di-lower alkylthio-lower alkyl is, for example, di-$C_1$–$C_4$alkylthio-$C_1$–$C_4$alkyl, for example dimethylthiomethyl, dipropylthiomethyl, 1,1- or 2,2-diethylthioethyl, diisopropylthiomethyl, dibutylthiomethyl or 3,3-dimethylthiopropyl.

Halogen is, for example, halogen having an atomic number of up to and including 35, such as chlorine or fluorine, also bromine.

Cycloalkyl is, for example, $C_3$–$C_8$cycloalkyl, especially $C_3$–$C_6$cycloalkyl, such as cyclopropyl, cyclobutyl, cyclopentyl or cyclohexyl.

Hydroxycycloalkyl is, for example, α-hydroxy-$C_3$–$C_6$cycloalkyl, such as 1-hydroxycyclopropyl, 1-hydroxycyclobutyl or 1-hydroxycyclohexyl.

Oxa- or thia-cycloalkyl is, for example, oxa- or thia-$C_3$–$C_8$cycloalkyl, especially oxa- or thia-$C_3$–$C_6$cycloalkyl, such as 2-oxacyclopropyl (oxiranyl), 2- or 3-oxacyclobutyl (oxetanyl), 2- or 3-thiacyclobutyl (thietanyl), 2- or 3-oxacyclopentyl (tetrahydrofuranyl), 2- or 3-thiacyclopentyl (thiolanyl) or 2-oxacyclohexyl (tetrahydropyranyl).

Dioxacycloalkyl is, for example, 1,3-dioxa-$C_3$–$C_8$cycloalkyl, such as 1,3-dioxolan-2-yl or 1,3-dioxan-2-yl.

Dithiacycloalkyl is, for example, 1,3-dithia-$C_3$–$C_8$cycloalkyl, such as 1,3-dithiolan-2-yl or 1,3-dithian-2-yl.

Cycloalkyl-lower alkyl is, for example, $C_3$–$C_8$-cycloalkyl-$C_1$–$C_4$alkyl, especially $C_3$–$C_6$-cycloalkyl-$C_1$–$C_4$alkyl, such as α-($C_3$–$C_6$cycloalkyl)-$C_1$–$C_4$alkyl, for example cyclopropylmethyl, cyclobutylmethyl, cyclopentylmethyl or cyclohexylmethyl.

Cycloalkenyl-lower alkyl is, for example, $C_3$–$C_8$cycloalkenyl-$C_1$–$C_4$alkyl, especially $C_3$–$C_6$cycloalkenyl-$C_1$–$C_4$alkyl, such as α-($C_3$–$C_6$cycloalkenyl)-$C_1$–$C_4$alky for example cyclopent-1-enylmethyl, cyclopent-2-enylmethyl, cyclopent-3-enylmethyl, cyclohex-1-enylmethyl, cyclohex-2-enylmethyl or cyclohex-3-enylmethyl.

Cycloalkyl(hydroxy)-lower alkyl is, for example, $C_3$–$C_6$cycloalkyl-$C_1$–$C_4$(hydroxy)alkyl, such as α-($C_3$–$C_6$cycloalkyl)-α-hydroxy-$C_1$–$C_4$alkyl, for example cyclopropyl(hydroxy)methyl, cyclobutyl(hydroxy)-methyl, or cyclohexyl(hydroxy)methyl.

(Lower alkylthiocycloalkyl)(hydroxy)-lower alkyl is, for example, 1-($C_1$–$C_4$alkylthio-$C_3$–$C_6$cycloalkyl)-1-hydroxy-$C_1$–$C_4$alkyl, such as (2-methylthiocycloprop-1-yl)hydroxymethyl.

Owing to their amphoteric character, the compounds of formula I are in the form of internal salts and can form both acid addition salts and salts with bases.

Acid addition salts of compounds of formula I are, for example, their pharmaceutically acceptable salts with suitable mineral acids, such as hydrohalic acids, sulfuric acid or phosphoric acid, for example hydrochlorides, hydrobromides, sulfates, hydrogen sulfates or phosphates, or salts with suitable aliphatic or aromatic sulfonic acids or N-substituted sulfamic acids, for example methanesulfonates, benzenesulfonates, p-toluenesulfonates or N-cyclohexylsulfamates (cyclamates).

Salts of compounds of formula I with bases are, for example, their salts with pharmaceutically acceptable bases, such as non-toxic metal salts derived from metals of groups Ia, Ib, IIa and IIb, for example alkali metal salts, especially sodium or potassium salts, alkaline earth metal salts, especially calcium or magnesium salts, and also ammonium salts with ammonia or organic amines or quaternary ammonium bases, such as unsubstituted or C-hydroxylated aliphatic amines, especially mono-, di- or tri-lower alkylamines, for example methyl-, ethyl- or diethyl-amine, mono-, di- or tri-(hydroxy-lower alkyl)amines, such as ethanol-, diethanol- or triethanolamine, tris(hydroxymethyl)methylamine or 2-hydroxy-tert-butylamine, or N-(hydroxy-lower alkyl)-N,N-di-lower alkylamines or N-(polyhydroxy-lower alkyl)-lower alkylamines, such as 2-(dimethylamino)ethanol or D-glucamine, or quaternary aliphatic ammonium hydroxides, for example tetrabutyl-ammonium hydroxide.

Provided asymmetric carbon atoms are present, the compounds according to the invention may be in the form of isomeric mixtures, especially in the form of racemates, or in the form of pure isomers, especially optical antipodes.

It has been found that the compounds of formula I and their pharmaceutically acceptable salts have valuable pharmacological properties. They exhibit an effective binding to the $GABA_B$ receptor and have been found to be antagonists of GABA ($\gamma$-aminobutyric acid) at that receptor. With regard to the mechanism, antagonism at $GABA_B$ receptors can increase the release of rapid stimulant amino acid transmitters, that is to say, glutamate and aspartate, and thus improve information processing in the brain. This is in keeping with the finding that the late post-synaptic inhibition potential in the hippocampus, which is attributed to a $GABA_B$ mechanism, is broken down by the antagonists and thus permits a faster nerve impulse transmission sequence.

It has also been found that chronic treatment with anti-depressants and repeated electric shocks increase the number of $GABA_B$ receptors in the cerebral cortex of rats. In accordance with receptor theories, chronic treatment with $GABA_B$ antagonists should have the same effect. For this and other reasons, $GABA_B$ antagonists can accordingly act as anti-depressants.

The $GABA_B$ antagonists according to the invention interact at the $GABA_B$ receptor with $IC_{50}$ values of approximately $10^{-8}$M (mole/liter) and above on cerebral cortex membranes of rats. In contrast to $GABA_B$ agonists, such as baclofen, they do not potentiate the stimulation by noradrenalin of adenylate cyclase on sections of the cerebral cortex of rats but act as antagonists of the baclofen action. The antagonism with respect to baclofen was also demonstrated on electrophysiological models in vitro, such as, for example, on the penicillin-induced "epileptic" hippocampus section preparation, where baclofen inhibits "epileptic-like" discharges from pyramidal cells at a concentration of 6 $\mu$M (micromole/liter). The compounds according to the invention act as antagonists of baclofen action at concentrations of from approximately 1 to approximately 100 nM (nanomole/liter). In vivo, it was possible to demonstrate the antagonism by the iontophoresis of baclofen at the cerebral cortex of rats and by the systemic use of antagonists in doses of from approximately 1 to approximately 100 mg/kg. At doses of from approximately 10 to approximately 30 mg/kg, antagonism towards the muscle-relaxing effect of baclofen occurs and is measured in the rotarod model.

The antagonists not only exhibit antagonism towards baclofen but also have an independent action as antagonists of endogenous GABA. Thus, the antagonists are active in conventional behavioural models that are typical of antidepressive, anxiolytic and/or nootropic properties. It was found that compounds of formula I, when administered orally, are active in the Swim Test according to Porsolt, in the Geller test, the delayed passive avoidance test (one-test modification) in pre-test and post-test situations, in the two-compartment test and in the complex labyrinth. In addition, in tests carried out on rhesus monkeys, an enhanced play instinct, curiosity and social grooming behaviour and a reduction in signs of anxiety were observed.

It was also established that the compounds of formula I and theft pharmaceutically acceptable salts have, in vivo, antiepileptic properties, especially a pronounced anti-absence action in the case of epileptic disorders of the "petit mal" type, that is to say, absence epilepsy in children and adolescents and atypical absences, such as the Lennox-Gastaut syndrome.

This can be demonstrated in a specific strain of rats by their pronounced inhibitory action on spontaneous "spike and wave" discharges in the animal model according to Vergnes M., Marescaux C., Micheletti G., Reis J., Depaulis A., Rumbach L. and Warter J. M., Neurosci. Lett. 33, 97–101 (1982).

The compounds of formula I and their pharmaceutically acceptable salts are accordingly outstandingly suitable as nootropics, antidepressants and anxiolytics, for example for the treatment of cerebral insufficiency symptoms, emotional depression, states of anxiety and epilepsy of the "petit mal" type, that is to say, absence epilepsy in children and adolescents, and also atypical absences, such as the Lennox-Gastaut syndrome, and as an antidote to baclofen.

The invention relates especially to compounds of formula I wherein

R is lower alkyl having at least 2 carbon atoms, lower alkenyl, lower alkynyl, oxo-lower alkyl, hydroxy- or dihydroxy-lower alkyl, hydroxy-lower alkenyl, mono-, di- or poly-halo-lower alkyl, mono-, di- or poly-halo-lower alkenyl, mono-, di- or poly-halo-(hydroxy)-lower alkyl, mono-, di- or poly-halo(hydroxy)-lower alkenyl, lower alkoxy-lower alkyl, di-lower alkoxy-lower alkyl, lower alkoxy(hydroxy)-lower alkyl, lower alkoxy(halo)-lower alkyl, lower alkylthio-lower alkyl, di-lower alkylthio-lower alkyl, cycloalkyl, hydroxycycloalkyl, oxa-, dioxa-, thia- and dithia-cycloalkyl, cycloalkyl-lower alkyl, cycloalkenyl-lower alkyl, cycloalkyl(-hydroxy)-lower alkyl, (lower alkylthio)cycloalkyl(hydroxy)-lower alkyl, or mono- or di-phenyl-lower alkyl that is unsubstituted or mono-, di- or tri-substituted by lower alkyl, lower alkoxy, halogen, hydroxy and/or by trifluoromethyl, naphthyl-lower alkyl or unsubstituted or halo-substituted thienyl-, furyl- or pyridyl-lower alkyl, $R_1$ is hydrogen or hydroxy, $R_2$ is a phenyl-, thienyl-, furyl- or pyridyl-lower alkyl radical that is mono- or di-substituted by carboxy;

lower alkoxycarbonyl; cyano; carbamoyl; N-mono- or N,N-di-lower alkylcarbamoyl; carboxy-lower alkyl; lower alkoxycarbonyl-lower alkyl; cyano-lower alkyl; carbamoyl-lower alkyl; N-mono- or N,N-di-lower alkylcarbamoyl-lower alkyl; or by oxazolyl, isoxazolyl, oxadiazolyl, triazolyl, tetrazolyl, oxazolyl-lower alkyl, isoxazolyl-lower alkyl, oxadiazolyl-lower alkyl, triazolyl-lower alkyl or tetrazolyl-lower alkyl, each of which is unsubstituted or substituted by lower alkyl, lower alkoxy, lower alkoxycarbonyl, cyano, hydroxy, amino or by halogen; and which phenyl-, thienyl-, furyl- or pyridyl-lower alkyl radical may be additionally substituted by lower alkoxy, polyfluoro-lower alkoxy, halogen or by polyfluoro-lower alkyl, and $R_3$ is hydrogen, lower alkyl or $R_2$, and the salts thereof, especially the pharmaceutically acceptable salts thereof.

The invention relates more especially to compounds of formula I wherein

R is $C_3$–$C_7$alkyl, such as propyl, isopropyl, butyl isobutyl or pentyl, $\alpha,\alpha$-di-$C_1$–$C_4$alkoxy-$C_1$–$C_4$alkyl, especially $\alpha,\alpha$-di-$C_1$–$C_4$alkoxymethyl, such as dimethoxy- or diethoxymethyl, $C_3$–$C_6$cycloalkyl-$C_1$–$C_4$alkyl, such as cyclopropyl- or cyclohexyl-methyl, $C_3$–$C_6$cycloalkenyl-$C_1$–$C_4$alkyl, such as cyclohex-3-enylmethyl, or is phenyl-$C_1$–$C_4$alkyl, such as benzyl, that is unsubstituted or mono-, di- or tri-substituted by $C_1$–$C_4$alkyl, such as methyl, $C_1$–$C_4$alkoxy, such as methoxy, hydroxy and/or by halogen, such as fluorine, chlorine or iodine, $R_1$ is hydrogen or hydroxy, $R_2$ is a phenyl-, thienyl-, furyl- or pyridyl-$C_1$–$C_4$alkyl radical that is mono- or di-substituted by carboxy; $C_1$–$C_4$alkoxycarbonyl, such as methoxy- or ethoxy-carbonyl; cyano; carbamoyl; N-mono- or N,N-di-$C_1$–$C_4$alkylcarbamoyl, such as methyl-, ethyl-, dimethyl-or diethyl-carbamoyl; carboxy-$C_1$–$C_4$alkyl, such as carboxymethyl, $C_1$–$C_4$alkoxycarbonyl-$C_1$–$C_4$alkyl, such as methoxy- or ethoxy-carbonylmethyl; cyano-$C_1$–$C_4$alkyl, such as cyanomethyl; carbamoyl-$C_1$–$C_4$alkyl, such as carbamoylmethyl; N-mono- or N,N-di-$C_1$–$C_4$alkylcarbamoyl-$C_1$–$C_4$alkyl, such as methyl-, ethyl-, dimethyl- or diethyl-carbamoylmethyl; or by the following, each of which is unsubstituted or substituted by $C_1$–$C_4$alkyl, such as methyl, $C_1$–$C_4$alkoxy, such as methoxy, $C_1$–$C_4$alkoxycarbonyl, such as methoxy- or ethoxy-carbonyl, cyano, hydroxy, amino or by halogen: oxazolyl, for example 5-$R_a$-oxazol-2-yl, isoxazolyl, for example 3-$R_a$-isoxazol-5-yl or 4-$R_a$-isoxazol-2-yl, oxadiazolyl, for example 3-$R_a$-1,2,4-oxadiazol-5-yl, 5-$R_a$-1,2,4-oxadiazol-3-yl or 5-$R_a$-1,3,4-oxadiazol-3-yl, triazolyl, for example 5-$R_a$- 1,2,4-triazol-3-yl or 3-$R_a$-1,2,4-triazol-5-yl, tetrazolyl, for example tetrazol-5-yl, oxazolyl-$C_1$–$C_4$alkyl, for example 5-$R_a$-oxazol-2-ylmethyl, isoxazolyl-$C_1$–$C_4$alkyl, for example 3-$R_a$-isoxazol-5-ylmethyl or 4-$R_a$-isoxazol-2-ylmethyl, oxadiazolyl-$C_1$–$C_4$alkyl, for example 3-$R_a$-1,2,4-oxadiazol-5-ylmethyl, 5-$R_a$-1,2,4-oxadiazol-3-ylmethyl or 5-$R_a$-1,3,4-oxadiazol-3-ylmethyl, triazolyl-$C_1$–$C_4$alkyl, for example 5-$R_a$-1,2,4-triazol-3-ylmethyl or 3-$R_a$-1,2,4-triazol-5-ylmethyl or tetrazolyl-$C_1$–$C_4$alkyl, for example tetrazol-5-ylmethyl, $R_a$ being hydrogen or, in the second place, $C_1$–$C_4$alkyl, such as methyl, $C_1$–$C_4$alkoxy, such as methoxy, $C_1$–$C_4$alkoxy-carbonyl, such as methoxy- or ethoxy-carbonyl, hydroxy, amino or halogen, such as chlorine; and which phenyl-, thienyl-, furyl- or pyridyl-$C_1$–$C_4$alkyl radical may be additionally substituted by $C_1$–$C_4$alkoxy, such as methoxy, polyfluoro-$C_1$–$C_4$alkoxy, such as trifluoromethoxy, halogen, such as fluorine, chlorine or bromine, or by polyfluoro-$C_1$–$C_4$alkyl, such as trifluoromethyl, and $R_3$ is hydrogen or $C_1$–$C_4$alkyl, such as methyl, and the salts thereof, especially the pharmaceutically acceptable salts thereof.

The invention relates especially to compounds of formula I wherein

R is $C_3$–$C_5$alkyl, such as butyl, $\alpha,\alpha$-di-$C_1$–$C_4$alkoxymethyl, such as diethoxymethyl, $C_3$–$C_6$cycloalkyl-$C_1$–$C_4$alkyl, such as cyclopropyl- or cyclohexyl-methyl, or benzyl, $R_1$ is hydrogen or hydroxy, $R_2$ is an $\alpha$-phenyl-$C_1$–$C_4$alkyl radical, such as a benzyl, 1-phenylethyl or 2-phenylprop-2-yl radical, or an $\alpha$-pyridyl-$C_1$–$C_4$alkyl radical, such as a pyridylmethyl radical, each of which radicals is mono- or di-substituted by carboxy, $C_1$–$C_4$alkoxycarbonyl, such as methoxy- or ethoxy-carbonyl, cyano, carbamoyl, carboxy-$C_1$–$C_4$alkyl, such as carboxymethyl, $C_1$–$C_4$alkoxycarbonyl-$C_1$–$C_4$alkyl, such as methoxy- or ethoxy-carbonylmethyl, cyano-$C_1$–$C_4$alkyl, such as cyanomethyl, carbamoyl-$C_1$–$C_4$alkyl, such as carbamoylmethyl, isoxazol-5-yl, isoxazol-2-yl, 1,2,4-oxadiazol-5-yl, 1,2,4-oxadiazol-3-yl, 1,3,4-oxadiazol-3-yl, 1,2,4-triazol-3-yl, 1,2,4-triazol-5-yl, tetrazol-5-yl, isoxazol-5-ylmethyl, isoxazol-2-ylmethyl, 1,2,4-oxadiazol-5-ylmethyl, 1,2,4-oxadiazol-3-ylmethyl, 1,3,4-oxadiazol-3-ylmethyl, 1,2,4-triazol-3-ylmethyl, 1,2,4-triazol-5-ylmethyl or by tetrazol-5-ylmethyl, and each of which radicals $\alpha$-phenyl-$C_1$–$C_4$alkyl and $\alpha$-pyridyl-$C_1$–$C_4$alkyl may be additionally substituted by $C_1$–$C_4$alkoxy, such as methoxy, trifluoromethoxy, halogen, such as fluorine, chlorine or bromine, or by trifluoromethyl, and $R_3$ is hydrogen, and the salts thereof, especially the pharmaceutically acceptable salts thereof.

The invention relates preferably to compounds of formula I wherein

R is $\alpha,\alpha$-di-$C_1$–$C_4$alkoxymethyl, such as diethoxymethyl, $C_3$–$C_6$cycloalkyl-$C_1$–$C_4$alkyl, such as cyclohexylmethyl, $C_3$–$C_6$cycloalk-3-enyl-$C_1$–$C_4$alkyl, such as cyclohex-3-enylmethyl, or benzyl, $R_1$ is hydroxy, $R_2$ is a phenyl-$C_1$–$C_4$alkyl radical, such as a benzyl, 1-phenylethyl or 2-phenylprop-2-yl radical, that is substituted by carboxy, cyano or by unsubstituted or amino- or halo-substituted 1,2,4-oxadiazol-5-yl, and $R_3$ is hydrogen, and the salts thereof, especially the pharmaceutically acceptable salts thereof.

The invention relates more especially to compounds of formula I wherein

R is $C_3$–$C_5$alkyl, such as butyl, $\alpha,\alpha$-di-$C_1$–$C_4$alkoxymethyl, such as diethoxymethyl, $C_3$–$C_6$cycloalkyl-$C_1$–$C_4$alkyl, such as cyclopropyl- or cyclohexyl-methyl, or benzyl, $R_1$ is hydrogen or hydroxy, $R_2$ is a phenyl-$C_1$–$C_4$alkyl radical, such as a benzyl, 1-phenylethyl or 2-phenylprop-2-yl radical, that is mono- or di-substituted by carboxy, $C_1$–$C_4$alkoxycarbonyl, such as methoxy- or ethoxy-carbonyl, cyano or by carbamoyl and may be additionally substituted by $C_1$-$C_4$alkoxy, such as methoxy, trifluoromethoxy, halogen, such as fluorine, chlorine or bromine, or by trifluoromethyl, and $R_3$ is hydrogen, and the salts thereof, especially the pharmaceutically acceptable salts thereof.

The invention relates preferably to compounds of formula I in which the carbon atom of the propylene chain that is bonded to the group $R_1$, if $R_1$ is hydroxy, and/or a chiral α-carbon atom of the aliphatic moiety of the radical $R_2$, if present, each have the (S) configuration.

The invention relates specifically to the compounds mentioned in the Examples and to the salts thereof, especially the pharmaceutically acceptable salts thereof.

The process for the preparation of the compounds of formula I provided according to the invention is carried out as follows: in a compound of formula II

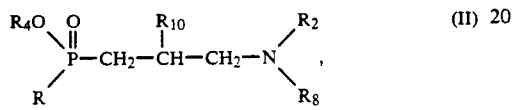

wherein $R_4$ is a hydroxy-protecting group, $R_8$ is a group $R_3$ or an amino-protecting group and $R_{10}$ is hydrogen or protected hydroxy, R, $R_1$, $R_2$ and $R_3$ being as defined, or in a salt thereof, the hydroxy groups are freed by replacing the hydroxy-protecting group $R_4$ by hydrogen and, where appropriate, the amino-protecting group $R_8$ is removed and, where appropriate, the protected hydroxy group $R_{10}$ is freed and, if desired, a resulting compound is converted into a different compound of formula I, an isomeric mixture obtainable according to the process is separated into its components and the preferred isomer is separated off and/or a free compound obtainable according to the process is converted into a salt or a salt obtainable according to the process is converted into the corresponding free compound.

Protected hydroxy groups $R_4O$, and also $R_{10}$, are, for example, etherified hydroxy groups, preferably hydroxy groups etherified by an aliphatic, cycloaliphatic, araliphatic or aromatic alcohol or by a silanol, especially lower alkoxy; lower alkenyloxy; phenoxy or phenylalkoxy, such as benzyloxy, that is unsubstituted or substituted, for example, by lower alkyl, lower alkoxy, halogen and/or by nitro; or tri-lower alkylsilyloxy, such as trimethylsilyloxy, tributylsilyloxy, or tert-butyl(dimethyl)silyloxy.

The replacement of the protecting group $R_4$ in the compounds of formula II by hydrogen can be effected by treatment with a suitable basic or acidic agent, such as an alkali metal hydroxide, for example sodium hydroxide or lithium hydroxide, an alkali metal halide, especially an alkali metal bromide or iodide, such as lithium bromide or sodium iodide, thiourea, an alkali metal thiophenolate, such as sodium thiophenolate, or a protonic acid or a Lewis acid, such as a mineral acid, for example hydrochloric acid, or a tri-lower alkylhalosilane, for example trimethylchlorosilane. The replacement reaction can be effected in the absence or presence of a solvent and, if necessary, with heating or with cooling in a closed vessel and/or under an inert gas atmosphere.

On the other hand, the replacement of the $R_4$ protecting group, for example a silyl or alkyl group, in compounds of formula II by hydrogen can also be carried out by treatment with an acid under hydrolytic conditions, especially with a mineral acid, such as a hydrohalic acid, for example hydrochloric acid, which is used in dilute or concentrated aqueous form, or by treatment with an organic silyl halide, such as trimethylsilyl iodide or bromide, and, if necessary, by subsequent hydrolysis. The reaction is preferably carried out at elevated temperature, for example by maintaining the reaction mixture at reflux temperature, and, where appropriate, using an organic diluent in a closed vessel and/or under an inert gas atmosphere. The method of replacing the protecting group $R_4$ depends, for example, on the type of substituent R contained in the compound of formula II and must be retained during the conversion of the compound II into a compound of formula I. The said conversion may be effected, for example, as in the illustrative Examples.

Amino-protecting groups $R_8$ in compounds of formula II can be removed by known processes which are chosen in accordance with the type of amino-protecting group, for example by solvolytic or hydrogenolytic processes, for example hydrolysis in the presence of an acid or base, acidolysis, for example treatment with trifluoroacetic acid, treatment with hydrazine, or hydrogenolysis in the presence of a metallic hydrogenation catalyst, or by some other suitable process.

Depending on the groups involved, the replacement and conversion may be effected in succession or simultaneously in accordance with methods known per se.

Preferably, all protecting groups, hydroxy-protecting groups $R_4$ and $R_{10}$, and amino-protecting groups $R_8$ are replaced by hydrogen in a single step by treatment with an acid, preferably with a hydrohalic acid, especially hydrochloric acid under hydrolytic conditions.

The starting materials of formula II can be prepared by various methods, for example as follows:

a) the group $R_2$ and, if desired, a radical $R_3$ other than hydrogen is(are) introduced into a compound of formula III

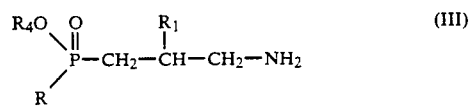

or b) a compound of formula IV

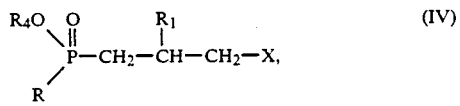

wherein X is a reactive esterified hydroxy group, or a salt thereof, is reacted with an amine of formula V

or c) a compound of formula VI

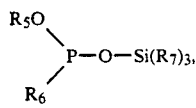

(VI)

wherein $R_5$ is a group $R_4$ or $-Si(R_7)_3$, $R_6$ is a radical R that is protected at a hydroxy group which may be present by a group $-Si(R_7)_3$ and the radicals $R_7$ are identical or different aliphatic hydrocarbon radicals, for example lower alkyl, especially methyl and/or tert-butyl, is condensed with a compound of formula VII

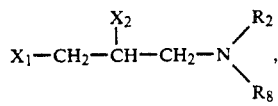

(VII)

wherein $X_1$ is reactive esterified hydroxy and $X_2$ is hydrogen or $X_1$ and $X_2$ together are epoxy and $R_8$ is a group $R_3$ or an amino-protecting group, or d) a compound of formula VIII

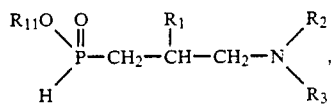

(VIII)

wherein $R_{11}$ is hydrogen or a group $R_4$, is reacted with a silylating agent and the resulting silyl-activated compound of formula IX

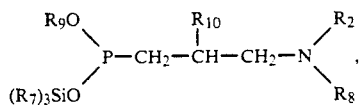

(IX)

wherein $R_8$ is a group $R_5$ other than hydrogen or is a group of the formula $-Si(R_7)_3$, $R_9$ is a group $R_4$ or a silyl-activated hydroxy group of the formula $-OSi(R_7)_3$ and $R_{10}$ is hydrogen or a group of the formula $-OSi(R_7)_3$, the radicals $R_7$ being identical or different aliphatic hydrocarbon radicals, for example lower alkyl, especially methyl and/or tert-butyl, is reacted with a reactive ester of an aliphatic, cycloaliphatic, cycloaliphatic-aliphatic or araliphatic alcohol, with an aliphatic, cycloaliphatic, cycloaliphatic-aliphatic, araliphatic or heteroarylaliphatic hydrocarbon that may additionally have a double bond in the $\alpha,\beta$-position, with an aliphatic, cycloaliphatic, cycloaliphatic-aliphatic, araliphatic or heteroarylaliphatic aldehyde or ketone or with an aliphatic epoxide, or e) for the preparation of a compound of formula II wherein $R_1$ is hydroxy, a compound of formula X

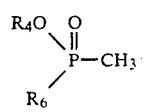

(X)

is reacted in the form of a metal salt of formula XI

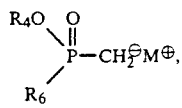

(XI)

wherein $R_6$ is a radical that is protected at a hydroxy group which may be present by a group $-Si(R_7)_3$, wherein the radicals $R_7$ are identical or different aliphatic hydrocarbon radicals, for example lower alkyl, especially methyl and/or tert-butyl, and $M^+$ is an alkali, alkaline earth or transition metal cation, with an aldehyde of formula XII

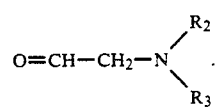

(XII)

If desired, a radical $R_3$ other than hydrogen may be introduced into an initially obtained compound of formula II wherein $R_3$ is hydrogen.

The introduction of the radical of formula $R_2$ in accordance with process variant a) is effected in customary manner, for example by reaction with a compound of formula $X-R_2$ (IIIa), wherein X is a reactive esterified hydroxy group, especially in the presence of a basic condensation agent, such as a tertiary organic base, for example a tri-lower alkylamine, for example triethylamine, triisopropylamine or tert-butyl(dimethyl)amine, or pyridyl, or a quaternery organic ammonium base, for example benzyl(trimethyl)ammonium hydroxide. Suitable reactive esterified hydroxy groups are preferably hydroxy groups esterified by a mineral acid, such as halogen, especially bromine, chlorine or iodine, or groups of the formula $R_2-O-SO_2-O-$.

The radical of formula $R_2$ can, however, also be introduced by reaction with a compound of the formula $O=R_2''$ (IIIb), wherein $R_2''$ is a divalent aralipatic or heteroarylaliphatic radical, the free valencies of which extend from the same carbon atom, under reductive conditions, especially in the presence of an alkali metal borohydride, for example sodium cyanoborohydride, preferably in a lower alkanol, such as ethanol, methanol or butanol.

The condensation of compounds of formula IV with amines of formula V in accordance with process variant b) is carried out in a manner analogous to that described above for the reaction of compounds of formulae III and IIIa.

In compounds of formula VII according to process variant c) reactive esterified hydroxy is preferably halogen, such as bromine, iodine or chlorine, or sulfonyloxy, such as lower alkanesulfonyloxy, for example methanesulfonyloxy, or unsubstituted or substituted benzenesulfonyloxy, for example benzene-, p-toluene- or p-bromobenzene-sulfonyloxy. Amino-protecting groups are especially silyl groups, for example of the formula $-Si(R_7)_3$, such as tri-lower alkylsilyl, for example trimethylsilyl. The reaction of compounds of formula VI and reactive esters VII can be carried out in a manner known per se, preferably under the conditions of the Arbusow reaction, advantageously in a temperature range of from approximately 60° C. to approximately 180° C., for example at from approximately 120° C. to approximately 160° C. In the case of the reaction of compounds of formula VI with epoxides (VII; $X_1+X_2$=epoxy), on the other hand, the operation is preferably carried out in the presence of a mild Lewis acid, especially zinc chloride, advantageously in an aprotic solvent.

Silylating agents that can be used according to process variant d) are especially tri-lower alkyl halosilanes of the formula $(R_7)_3Si$-Hal (VIIIa), wherein $R_7$ is lower alkyl and Hal is halogen, such as chlorine, bromine or iodine, such as trimethylchlorosilane or trimethylbromosilane, or hexa-lower alkyldisilazanes of the formula $(R_7)_3Si$—NH—$Si(R_7)_3$ (VIIIb), wherein $R_7$ is lower alkyl, such as hexamethyldisilazane. The silyl-activated intermediate is preferably a compound of formula IXa

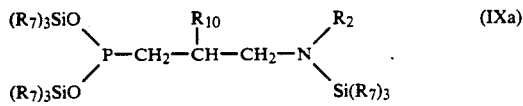

The reaction of the intermediate of formula IX or IXa with the component introducing the radical R is carried out preferably in the presence of a basic condensation agent, such as a tertiary organic base, for example a tri-lower alkylamine, for example triethylamine, triisopropylamine or tert-butyl(dimethyl)amine, or pyridine, or a quaternary organic ammonium base, for example benzyl(trimethyl)ammonium hydroxide.

In starting materials of formula X for process variant e), transition metal cations are, for example, lithium, sodium or potassium cations or groups of the formula —Mg-Hal or —Zn-Hal, wherein Hal is chlorine, bromine or iodine. The condensation of compounds of formulae XI and XII is carried out in the manner customary for such organo-metal reactions.

The introduction of a radical $R_3$ other than hydrogen is carried out in customary manner, especially in the manner indicated under process variant a).

In starting materials, for example of formulae II, V, VII, VIII, IX and XII, esterified carboxy groups or cyano groups as constituents of the radical $R_2$ can be incorporated into one of the ring systems mentioned at the beginning. Thus, esterified carboxy bonded directly or by way of a spacer can be converted into the corresponding compound of formula I having a 3-$R_a$-1,2,4-oxadiazol-5-yl group that is bonded directly or by way of a spacer by reaction with a corresponding hydroxamic acid of the formula $R_aC(=NOH)$—$NH_2$, wherein $R_a$ is, for example, lower alkyl or unsubstituted or lower alkylated amino, for example in the presence of sodium and pulverised molecular sieves in a lower alkanol, such as ethanol. In an analogous manner, cyano can be converted by treatment with hydroxylamine hydrochloride in the presence of potassium carbonate/ethanol into a hydroxamic acid group which can be convened by condensation with an anhydride of the formula $(R_aCO)_2O$, such as acetic anhydride, into the corresponding 3-$R_a$-1,2,4-oxadiazol-5-yl group, such as a 3-methyl-1,2,4-oxadiazol-5-yl group. Analogously, cyano can be convened by reaction with a hydroxamic acid of the formula $R_aC(=NOH)$—$NH_2$, wherein $R_a$ is, for example, lower alkyl or unsubstituted or lower alkylated amino, into 3-$R_a$-1,2,4-triazol-5-yl.

In general, it is possible, starting from compounds of formula I wherein $R_2$ has a carboxy or cyano group bonded directly or by way of a spacer, to convert the carboxy or cyano group by customary methods of ring formation into oxazolyl, for example 4-$R_a$-oxazol-2-yl, isoxazolyl, for example 3-$R_a$-isoxazol-5-yl, oxadiazolyl, for example 5-$R_a$-1,2,4-oxadiazol-3-yl or 5-$R_a$-1,3,4-oxadiazol-3-yl, triazolyl, for example 5-$R_a$-1,2,4-triazol-3-yl or tetrazolyl, for example tetrazol-5-yl, each of which is unsubstituted or substituted by lower alkyl, lower alkoxy, lower alkoxycarbonyl, cyano, hydroxy, amino or by halogen, $R_a$ being hydrogen or, in the second place, lower alkyl, lower alkoxy, lower alkoxycarbonyl, hydroxy, amino or halogen. For example, esterified carboxy can be converted into a 5-$R_a$-oxazol-2-yl group by reaction with an oxime of the formula $R_a$-$C(CH_3)=N$—OH in tetrahydrofuran and in the presence of sulfuric acid.

In starting materials, for example of the formulae II, V, VII, VIII, IX and XII, and resulting compounds in which $R_2$ has a 3-amino-1,2,4-oxadiazol-5-yl group that is bonded directly or by way of a spacer, the 3-amino group of the same can be replaced in customary manner by halogen, for example by treatment with sodium nitrite in the presence of a hydrohalic acid, or by cyano by treatment with amyl nitrite. In an analogous manner, halogen can be replaced by etherified hydroxy, for example by lower alkoxy by reaction with an alkali metal lower alkanolate.

Resulting compounds of formula I can be convened in a manner known per se into other compounds of formula I.

For example, a radical $R_3$ other than hydrogen can be introduced into compounds of formula I wherein $R_3$ is hydrogen, the procedure being, for example, analogous to that described under process variant a).

In addition, free and functionally modified carboxy groups in compounds of formula I can be converted into one another in customary manner. For example, esterified or amidated carboxy groups, or carboxy or cyano groups incorporated into a heteroaromatic ring system, can be hydrolysed to form carboxy in the presence of an acidic agent or, especially, a basic agent, such as an alkali metal hydroxide, for example lithium hydroxide.

In resulting compounds in which $R_2$ has a 3-amino-1,2,4-oxadiazol-5-yl group that is bonded directly or by way of a spacer, the 3-amino group of the same can be replaced in customary manner by halogen, for example by treatment with sodium nitrite in the presence of a hydrohalic acid, or by cyano by treatment with amyl nitrite. In an analogous manner, halogen can be replaced by etherified hydroxy, for example by lower alkoxy by reaction with an alkali metal lower alkanolate.

Resulting salts can be converted into the free compounds in a manner known per se, for example by treatment with a base, such as an alkali metal hydroxide, a metal carbonate or metal hydrogen carbonate, or ammonia, or another of the salt-forming bases mentioned at the beginning, or with an acid, such as a mineral acid, for example with hydrochloric acid, or another of the salt-forming acids mentioned at the beginning.

Resulting salts can be converted into different salts in a manner known per se; for example, acid addition salts can be converted by treatment with a suitable metal salt, such as a sodium, barium or silver salt, of another acid in a suitable solvent in which an inorganic salt being formed is insoluble and is thus excluded from the reaction equilibrium, and base salts can be converted by freeing the free acid and converting into a salt again.

The compounds of formula I, including their salts, may also be obtained in the form of hydrates or may include the solvent used for crystallisation.

Owing to the close relationship between the novel compounds in free form and in the form of their salts, hereinbefore and hereinafter the free compounds and their salts are also optionally to be understood as being the corresponding salts and free compounds, respectively, where appropriate and where the context so allows.

Resulting diastereoisomeric mixtures and mixtures of racemates can be separated in known manner into the pure diastereoisomers and racemates, respectively, on the basis of the physico-chemical differences between their constituents, for example by chromatography and/or fractional crystallisation.

Resulting racemates can also be resolved into the optical antipodes by known methods, for example by recrystallisation from an optically active solvent, with the aid of microorganisms or, by reaction of the resulting diastereoisomeric mixture or racemate with an optically active auxiliary compound, for example according to the acidic, basic or functionally modifiable groups contained in compounds of formula I, with an optically active acid, base or an optically active alcohol, into mixtures of diastereoisomeric salts or functional derivatives, such as esters, separation of the same into the diastereoisomers from which the desired enantiomer can be freed in customary manner. Suitable bases, acids and alcohols for the purpose are, for example, optically active alkaloid bases, such as strychnine, cinchonine or brucine, or D- or L-(1-phenyl)ethylamine, 3-pipecoline, ephedrine, amphetamine and similar bases that can be obtained by synthesis, optically active carboxylic or sulfonic acids, such as quinic acid or D- or L-tartaric acid, D- or L-di-o-toluoyltartaric acid, D- or L-malic acid, D- or L-mandelic acid, or D- or L-camphorsulfonic acid, or optically active alcohols, such as borneol or D- or L-(1-phenyl)ethanol.

The invention relates also to those forms of the process according to which a compound obtainable as intermediate at any stage of the process is used as starting material and the remaining steps are carried out, or a starting material is used in the form of a salt or, especially, is formed under the reaction conditions.

The invention relates also to the novel starting materials which have been specifically developed for the preparation of the compounds according to the invention, especially the group of starting materials that lead to the compounds of formula I mentioned at the beginning as being preferred, to the processes for their preparation and to their use as intermediates.

The novel compounds of formula I may be used, for example, in the form of pharmaceutical compositions that comprise a therapeutically effective amount of the active ingredient, where appropriate together with inorganic or organic, solid or liquid, pharmaceutically acceptable carriers that are suitable for enteral, for example oral, or parenteral administration. For example, tablets or gelatin capsules are used that contain the active ingredient together with diluents, for example lactose, dextrose, saccharose, mannitol, sorbitol, cellulose and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat, rice or arrowroot starch, gelatin, tragacanth, methylcellulose, sodium carboxymethylcellulose and/or polyvinylpyrrolidone, and, if desired, disintegrators, for example starches, agar, alginic acid or a salt thereof, for example sodium alginate, and/or effervescent mixtures, or absorbents, colourings, flavourings and sweeteners. The novel compounds of formula I can also be used in the form of parenterally administrable compositions or in the form of infusion solutions. Such solutions are preferably isotonic aqueous solutions or suspensions which, for example in the case of lyophilised compositions that comprise the active ingredient on its own or together with a carrier, for example mannitol, can be prepared before use. The pharmaceutical compositions may be sterilised and/or may comprise excipients, for example preservatives, stabilisers, wetting agents and/or emulsifiers, solubilisers, salts for regulating the osmotic pressure and/or buffers. The present pharmaceutical compositions which, if desired, may comprise other pharmacologically active substances, are prepared in a manner known per se, for example by conventional mixing, granulating, confectioning, dissolving or lyophilising processes, and comprise approximately from 0.1% to 100%, especially from approximately 1% to approximately 50%, and, in the case of lyophilisates, up to approximately 100%, active ingredient.

The invention relates also to the use of the compounds of formula I, preferably in the form of pharmaceutical compositions.

The dose may depend on various factors, such as the mode of administration, species, age and/or individual condition. The doses to be administered daily are, in the case of oral administration, from approximately 1 to approximately 50 mg/kg, especially from 5 to approximately 25 mg/kg, and, in the case of warm-blooded animals having a body weight of approximately 70 kg, preferably from approximately 70 mg to approximately 3500 mg, especially from approximately 350 to approximately 1750 mg, expediently divided into from 2 to 6, for example 3 or 4, single doses.

The following Examples serve to illustrate the invention; temperatures are given in degrees Celsius and pressures in mbar.

EXAMPLE 1

0.97 g of trimethylbromosilane is added to a solution of 0.62 g of 3-{N-[1-(3-cyanophenyl)ethyl]amino}-2(S)-hydroxy-propyl(cyclohexylmethyl)phosphinic acid ethyl ester in 10 ml of absolute dichloromethane. The resulting solution is stirred for 24 hours at room temperature, the volatile portions are removed under reduced pressure and the residue is dissolved in 99.9% methanol. The solution is stirred for 1 hour at room temperature, the solvent is removed and the residue is crystallised from ethanol to give 3-{N-[1-(3-cyanophenyl)ethyl]amino}-2(S)-hydroxy-propyl(cyclohexylmethyl)phosphinic acid hydrobromide having a melting point of 209°–210°.

The starting material can be prepared, for example, as follows:

21 g of 99% sodium hydride are suspended at room temperature under argon in 1000 ml of anhydrous tetrahydrofuran, and a solution of 172.2 g of 1,1-diethoxyethylphosphinic acid ethyl ester is added dropwise over a period of 2.5 hours, the temperature being maintained at from 20° to 25°. The reaction is exothermic and involves the evolution of gas. The batch is then stirred for 1.5 hours at room temperature, 142.2 g of bromomethylcyclohexane are added and heating under reflux is effected for 24 hours. The suspension is cooled to 4° and 250 ml of water are carefully added. Two phases are formed. The tetrahydrofuran phase is separated off and the aqueous phase is extracted twice with 250 ml of dichloromethane each time. Concentration by evaporation yields a brown oil which, after distillation under reduced pressure, gives 1,1-diethoxyethyl(cyclohexylmethyl)phosphinic acid ethyl ester having a boiling point of 95° ($1.8 \times 10^{-4}$ mbar).

150 g of trimethylchlorosilane are added to a solution of 213 g of 1,1-diethoxyethyl(cyclohexylmethyl)phosphinic acid ethyl ester in 600 ml of a mixture of dichloromethane and ethanol (90:10% by volume) and the batch is stirred for 2 to 3 days at room temperature. The solvent is removed and the residue is distilled under reduced pressure to give P-(cyclohexylmethyl)phosphinic acid ethyl ester having a boiling point of 50° ($2 \times 10^{-4}$ mbar).

32 g of trimethylchlorosilane are added to a solution of 51.0 g of P-(cyclohexylmethyl)phosphinic acid ethyl ester in 750 ml of absolute tetrahydrofuran and 29.8 g of triethylamine. A white precipitate is formed. The resulting suspension is stirred for 24 hours at room temperature, filtered under argon and concentrated by evaporation. 24 g of (R)-epichlorohydrin and 6.6 g of anhydrous zinc chloride are added to the colourless oil that remains. The reaction is strongly exothermic and when it has subsided the reaction mixture is heated for 24 hours at 60° and then cooled to room temperature. 250 ml of dichloromethane are added and the batch is washed with water. The organic phase is separated off, dried over sodium sulfate and concentrated by evaporation. The residue is taken up in a mixture of 99 ml of methanol and 1 ml of acetic acid and the batch is stirred for 24 hours at room temperature and concentrated by evaporation. The residue is chromatographed on silica gel to give 3-chloro-2(R)-hydroxy-propyl(cyclohexylmethyl)phosphinic acid ethyl ester in the form of a colourless oil.

A mixture of 5.65 g of 3-chloro-2(R)-hydroxy-propyl(cyclohexylmethyl)phosphinic acid ethyl ester, 2.92 g of N-[1-(3-cyanophenyl)ethyl]amine, 2.60 g of Hünig base and 10 ml of ethanol is heated under reflux for 5 days, then cooled to room temperature and concentrated by evaporation. Chromatography of the residue on silica gel gives 3-{N-[1-(3-cyanophenyl)ethyl]amino}-2(S)-hydroxy-propyl(cyclohexylmethyl)phosphinic acid ethyl ester in the form of an oil; $[\alpha]_D^{20}$ = +8.6 0.8(c=1.225 in trichloromethane).

EXAMPLE 2

A solution of 0.4 g of lithium hydroxide in 10 ml of water is added to a solution of 3.0 g of 3-{N-[1-(3-cyanophenyl)ethyl]amino}-2(S)-hydroxy-propyl(cyclohexylmethyl)phosphinic acid ethyl ester in 10 ml of ethanol and the batch is heated under reflux for 24 hours. It is cooled to 4° and neutralised with aqueous phosphoric acid. The solvent is removed and the residue is taken up in warm methanol and filtered. Removal of the solvent and crystallisation from ethanol/acetone gives lithium 3-{N-[1-(3-carboxyphenyl)ethyl]amino}-2(S)-hydroxy-propyl(cyclohexylmethyl)phosphinate having a melting point of 160°-184°.

EXAMPLE 3

In a manner analogous to that described in Example 1, there is obtained, by reacting 3-chloro-2(R)-hydroxypropyl(cyclohexylmethyl)phosphinic acid ethyl ester with 1-(3-methoxycarbonylphenyl)ethylamine, lithium 3-{N-[1-(3-carboxyphenyl)ethyl]amino}-2(S)-hydroxypropyl(cyclohexylmethyl)phosphinate having a melting point of 160°-184°, which is identical with the product of Example 2.

EXAMPLE 4

In a manner analogous to that described in Example 1 there are obtained
a) 3-{N-[1-(4-cyanophenyl)ethyl]amino}-2(S)-hydroxy-propyl(cyclohexylmethyl)phosphinic acid of m.p. 204°-209°;
b) 3-{N-[1(S)-(4-cyanophenyl)ethyl]amino}-2(S)-hydroxy-propyl(cyclohexylmethyl)phosphinic acid hydrobromide of m.p. 217°-218°;
c) 3-{N-[1(R)-(4-cyanophenyl)ethyl]amino}-2(S)-hydroxy-propyl(cyclohexylmethyl)phosphinic acid hydrobromide of m.p. 210°-212°;
d) 3-{N-[1(S)-(3-cyanophenyl)ethyl]amino 56 -2(S)-hydroxy-propyl(cyclohexylmethyl)phosphinic acid hydrobromide of m.p. 224°-225°;
e) 3-{N-[1(S)-(3-cyanophenyl)ethyl]amino}-2(R)-hydroxy-propyl(cyclohexylmethyl)phosphinic acid hydrobromide of m.p. 168°-170°;
f) 3-{N-[1(R)-(3-cyanophenyl)ethyl]amino}-2(S)-hydroxy-propyl(cyclohexylmethyl)phosphinic acid hydrobromide of 220°-222°.

EXAMPLE 5

In a manner analogous to that described in Example 2 there are obtained
a) 3-{N-[1-(4-carboxyphenyl)ethyl]amino}-2(S)-hydroxy-propyl(cyclohexylmethyl)phosphinic acid of m.p. 180°-187°;
b) lithium 3-{N-[1(S)-(4-carboxyphenyl)ethyl]amino}-2(S)-hydroxy-propyl(cyclohexylmethyl)phosphinate of m.p. 184°-186°;
c) lithium 3-{N-[1(R)-(4-carboxyphenyl)ethyl]amino}-2(S)-hydroxy-propyl(cyclohexylmethyl)phosphinate of m.p. 190°-192°;
d) lithium 3-{N-[1(S)-(3-carboxyphenyl)ethyl]amino}-2(S)-hydroxy-propyl(cyclohexylmethyl)phosphinate of m.p. 180°-182°;
e) lithium 3-{N-[1(S)-(3-carboxyphenyl)ethyl]amino}-2(R)-hydroxy-propyl(cyclohexylmethyl)phosphinate of m.p. 184°-186°;
f) lithium 3-{N-[1(R)-(3-carboxyphenyl)ethyl]amino}-2(S)-hydroxy-propyl(cyclohexylmethyl)phosphinate of m.p. 181°-183°;
g) lithium 3-{N-[1(R)-(3-carboxyphenyl)ethyl]amino}-2(S)-hydroxy-propyl(cyclohex-3-enylmethyl)phosphinate;
h) lithium 3-{N-[1(S)- (4-carboxyphenyl)ethyl]amino}-2(S)-hydroxy-propyl(cyclohex-3-enylmethyl)phosphinate.

EXAMPLE 6

In a manner analogous to that described in Example 1 there are obtained
a) 3-{N-[1-(4-cyanophenyl)ethyl]amino}-2(S)-hydroxy-propyl(benzyl)phosphinic acid of m.p. 110°-120°;
b) 3-{N-[1-(3-cyanophenyl)ethyl]amino}-2(S)-hydroxy-propyl(benzyl)phosphinic acid hydrobromide of m.p. 134°-138°.

EXAMPLE 7

In a manner analogous to that described in Example 2 there are obtained a) 3-{N-[1-(4-carboxyphenyl)ethyl]amino}-2(S)-hydroxy-propyl(benzyl)phosphinic acid of m.p. 188°–191°;

b) lithium 3-{N-[1-(3-carboxyphenyl)ethyl]amino}-2(S)-hydroxy-propyl(benzyl)phosphinate of m.p. 185°–190°;

c) 3-{N-[1-(3-carboxy-4-methoxyphenyl)ethyl]amino}-2(S)-hydroxy-propyl(benzyl)phosphinic acid.

EXAMPLE 8

In a manner analogous to that described in Examples 1 to 3, it is also possible to prepare:

3-{{N-{1-[3-(isoxazol-5-yl)phenyl]ethyl}amino}}-2(S)-hydroxy-propyl(cyclohexylmethyl)phosphinic acid;

3-{{N-{1-[3-(isoxazol-2-yl)phenyl]ethyl}amino}}-2(S) hydroxy-propyl(cyclohexylmethyl)phosphinic acid;

3-{{N-{1-[3-(1,2,4-oxadiazol-5-yl)phenyl]ethyl}amino}}-2(S)-hydroxy-propyl(cyclohexylmethyl)phosphinic acid;

3-{{N-{1-[3-(1,2,4-oxadiazol-3-yl)phenyl]ethyl}amino}}-2(S)-hydroxy-propyl(cyclohexylmethyl)phosphinic acid;

3-{{N-{1-[3-(1,2,4-triazol-3-yl)phenyl]ethyl}amino}}-2(S)-hydroxy-propyl(cyclohexylmethyl)phosphinic acid;

3-{{N-{1-[3-(1,2,4-triazol-5-yl)phenyl]ethyl}amino}}-2(S)-hydroxy-propyl(cyclohexylmethyl)phosphinic acid;

3-{{N-{1-[3-(tetrazol-5-yl)phenyl]ethyl}amino}}-2(S)-hydroxy-propyl(cyclohexylmethyl)phosphinic acid;

3-{{N-{1-[4-(3-amino-1,2,4-oxadiazol-5-yl)phenyl]ethyl}amino}}-2(S)-hydroxy-propyl(cyclohexylmethyl)phosphinic acid;

3-{{N-{1-[4-(3-amino-1,2,4-oxadiazol-5-yl)phenyl]ethyl}amino}}-2(S)-hydroxy-propyl(benzyl)phosphinic acid;

3-{N-[1-(4-carboxymethylphenyl)ethyl]amino}-2(S)-hydroxy-propyl(cyclohexylmethyl)phosphinic acid;

3-{N-[1-(2-carboxymethylpyrid-4-yl)ethyl]amino}-2(S)-hydroxy-propyl(cyclohexylmethyl)phosphinic acid;

3-{N-[1-(4-carboxymethylphenyl)ethyl]amino}-2(S)-hydroxy-propyl(cyclohexylmethyl)phosphinic acid and 3-{N-[1-(4-carboxymethylphenyl)ethyl]amino}-2(S)-hydroxy-propyl(benzyl)phosphinic acid.

EXAMPLE 9

In a manner analogous to that described in Example 2 there are obtained a) lithium 3-{N-[1-(R)-(3-carboxyphenyl)ethyl]amino}-2-(S)-hydroxy-propyl(diethoxymethyl)phosphinate, m.p. 166°–168°;

b) lithium 3-{N-[1-(S)-(3-carboxyphenyl)ethyl]amino}-2-(S)-hydroxy-propyl(diethoxymethyl)phosphinate, m.p. 168°–170°.

EXAMPLE 10

A solution of 27 mg of lithium hydroxide is added to a solution of 0.25 g of 3-{{N-{1-[4-(3-amino-1,2,4-oxadiazol-5-yl)phenyl}amino}}-2(S)-hydroxy-propyl(cyclohexylmethyl)phosphinic acid ethyl ester in 1 ml of ethanol and the batch is heated under reflux for 24 hours. It is then allowed to cool to room temperature and is adjusted to a pH of 7 with concentrated phosphoric acid. A white precipitate is formed. The suspension of the same is concentrated to dryness by evaporation, the residue is taken up in methanol and filtration is carried out. The clear filtration solution is left to stand for 24 hours at 4°. Crystals are precipitated which are isolated by filtration and dried under reduced pressure to give 3-{{N-{1-[4-(3-amino-1,2,4-oxadiazol-5-yl)phenyl}amino}}-2(S) hydroxy-propyl(cyclohexylmethyl)phosphinic acid in the form of yellow crystals having a melting point of 222.5°–224°; mass spectrum: $M^+ - = 422$; $^1$H-NMR spectrum (CD$_3$OD), $\delta$(ppm)=8.14 (2H,m), 7.68 (2H,m), 4.50(1H,m), 4.20 (1H,m), 3.19 (1H,dd), 3.02 (1H,dd), 2.10–1.54 (12H,m), 1.39–0.95 (6H,m).

The starting material can be prepared, for example, as follows:

10 g of 4-acetylbenzoic acid ethyl ester and 40 g of ammonium acetate are dissolved in 210 ml of absolute methanol, and 3.63 g of sodium cyanoborohydride are added. The reaction solution is stirred for 24 hours at room temperature, cooled to 4° and adjusted to a pH of 1 by the addition of concentrated hydrochloric acid. The methanol is removed under reduced pressure and the suspension that remains is filtered. The aqueous filtrate is washed with diethyl ether, adjusted to a pH of 10 at 4° by the addition of solid sodium hydroxide and extracted with diethyl ether. Drying is carried out over sodium sulfate and is followed by concentration to dryness by evaporation under reduced pressure, and the oil that remains is distilled under reduced pressure to give 1-(4-carboxyphenyl)ethylamine having a boiling point of 130°–140° (6×10$^{-2}$ mbar).

0.8 g of sodium is dissolved in 60 ml of absolute ethanol, and 12 g of molecular sieve (4Å) and 2.63 g of N-hydroxyguanidine are added. The batch is stirred for 1 hour at room temperature and then 1.14 g of 1-(4-carboxyphenyl)ethylamine are added. The resulting turbid yellowish solution is heated under reflux for 2 hours after which time it can be established by thin layer chromatography that the reaction is complete. The batch is filtered and the solvent is removed under reduced pressure. The residue is digested in water and cooled in an ice bath, and then the precipitate is isolated by filtration, washed with a small amount of water and dried under reduced pressure to give 1-[4-(3-amino-1,2,4-oxadiazol-5-yl)phenyl]ethylamine having a melting point of 150°–151°.

A solution of 0.8 g of 1-[4-(3-amino-1,2,4-oxadiazol-5-yl)phenyl]ethylamine and 1.106 g of 3-chloro-2(R)-hydroxy-propyl(cyclohexylmethyl)phosphinic acid ethyl ester in 5 ml of ethanol, containing 0.5 g of Hünig base, is heated under reflux for 24 hours. It is then cooled to room temperature and the solvent is removed under reduced pressure. Chromatography of the residue of concentration by evaporation on silica gel gives 3-{{N-{1-[4-(3-amino-1,2,4-oxadiazol-5-yl)phenyl}amino}}-2(S)-hydroxy-propyl(cyclohexylmethyl)phosphinic acid ethyl ester in the form of a pale yellow solid; mass spectrum: $M^+ - 1 = 449$; $^1$H-NMR spectrum (CD₃OD), δ(ppm)=8.00 (2H,m), 7.45 (2H,m), 4.21–3.92 (3H,m), 3.80 (1H,m), 2.70–2.30 (2H,m), 2.00–1.55 (9H,m), 1.40–0.90 (8H,m).

EXAMPLE 11

20 mg of 5% palladium-on-carbon are added to a solution of 0.125 g of lithium 3-{N-[1(R)-(3-carboxyphenyl)ethyl]amino}-2(S)-hydroxy-propyl(cyclohex-3-enylmethyl)phosphinate in 5 ml of ethanol and the batch is hydrogenated at room temperature and normal pressure for 15 minutes. The catalyst is filtered off through Celite ® and the filtrate is adjusted to a pH of 1 with ethanolic hydrochloric acid. Removal of the solvent and recrystallisation from isopropanol gives lithium 3-{N-[1(R)-(3-carboxyphenyl)ethyl]amino}-2(S)-hydroxy-propyl(cyclohexylmethyl)phosphinate, which is identical with the compound of Example 5(f).

Lithium 3-{N-[1(S)-(4-carboxyphenyl)ethyl]amino}-2(S)-hydroxy-propyl(cyclohex-3-enylmethyl)phosphinate, which is identical with the compound of Example 5(g), can also be prepared in an analogous manner.

EXAMPLE 12

In a manner analogous to that described in Example 10, it is also possible to prepare:

3-{{N-{1-[4-(3-amino-1,2,4-oxadiazol-5-yl)phenyl]}amino}}-2(S)-hydroxy-propyl(benzyl)phosphinic acid;

3-{{N-{1-[3-(3-amino-1,2,4-oxadiazol-5-yl)phenyl]}amino}}-2(S)-hydroxy-propyl(benzyl)phosphinic acid;

3-{{N-{1-[3-(3-amino-1,2,4-oxadiazol-5-yl)phenyl]}amino}}-2(S )-hydroxy-propyl(cyclohexylmethyl)phosphinic acid;

3-{{N-{1-[3-(3-chloro-1,2,4-oxadiazol-5-yl)phenyl]}amino}}-2(S)-hydroxy-propyl(cyclohexylmethyl)phosphinic acid;

3-{{N-{1-[3-(3-chloro-1,2,4-oxadiazol-5-yl)phenyl]}amino}}-2(S)-hydroxy-propyl(benzyl)phosphinic acid;

3-{{N-{1-[4-(3-chloro-1,2,4-oxadiazol-5-yl)phenyl]}amino}}-2(S)-hydroxy-propyl(benzyl)phosphinic acid;

3-{{N-{1-[4-(3-chloro-1,2,4-oxadiazol-5-yl)phenyl]}amino}}-2(S)-hydroxy-propyl(cyclohexylmethyl)phosphinic acid;

3-{{N-{1-[4-(1,2,4-oxadiazol-5-yl)phenyl}amino}}-2(S)-hydroxy-propyl(cyclohexylmethyl)phosphinic acid;

3-{{N-{1-[4-(1,2,4-oxadiazol-5-yl)phenyl}amino}}-2(S)-hydroxy-propyl(benzyl)phosphinic acid;

3-{{N-{1-[3-(1,2,4-oxadiazol-5-yl)phenyl}amino}}-2(S)-hydroxy-propyl(cyclohexylmethyl)phosphinic acid;

3-{{N-{1-[3-(1,2,4-oxadiazol-5-yl)phenyl}amino}}-2(S)-hydroxy-propyl(benzyl)phosphinic acid;

3-{N-[1-(3-carboxy-4-methoxyphenyl)ethyl]amino}-2(S)-hydroxy-propyl(pyrid-3-yl-methyl)phosphinic acid;

3-{N-[1-(3-carboxy-4-methoxyphenyl)ethyl]amino}-2(S)-hydroxy-propyl(thien-2-yl-methyl)phosphinic acid;

3-{N-[1-(3-carboxy-4-methoxyphenyl)ethyl]amino}-2(S)-hydroxy-propyl(fur-2-yl-methyl)phosphinic acid.

EXAMPLE 13

A solution of 1.0 g of lithium 3-{N-[1(S)-(3-carboxyphenyl)ethyl]amino}-2(S)-hydroxy-propyl(cyclohexylmethyl)phosphinate in 2 ml of water is applied to a DOWEX ® 50 W×8 ion exchange column (40–60 mesh) and eluted with water. The ninhydrin-positive fractions are combined and concentrated to dryness by evaporation under reduced pressure. Crystallisation of the foamy residue of concentration by evaporation from ethanol/tetrahydrofuran gives 3-{N-[1(S)-(3-carboxyphenyl)ethyl]amino}-2(S)-hydroxy-propyl(cyclohexylmethyl)phosphinic acid having a melting point of 225°–228°.

EXAMPLE 14

Tablets, each comprising 200 mg of 3-{N-[1-(3-cyanophenyl)ethyl]amino}-2(S)-hydroxy-propyl(cyclohexylmethyl)phosphinic acid or a salt thereof, can be prepared as follows:

| Composition (10 000 tablets) | |
|---|---|
| active ingredient | 2000.0 g |
| lactose | 500.0 g |
| potato starch | 352.0 g |
| gelatin | 8.0 g |
| talc | 60.0 g |
| magnesium stearate | 10.0 g |
| silica (highly dispersed) | 20.0 g |
| ethanol | q.s. |

The active ingredient is mixed with the lactose and 292 g of potato starch, the mixture is moistened with an ethanolic solution of the gelatin and granulated through a sieve. After drying, the remainder of the potato starch, the magnesium stearate, the talc and the silica are mixed in and the mixture is compressed to form tablets each weighing 295.0 mg and each comprising 50.0 mg of active ingredient which, if desired, may be provided with dividing notches for finer adjustment of the dose.

EXAMPLE 15

Film-coated tablets, each comprising 400 mg of 3-}N-[1-(3-cyanophenyl)ethyl]amino}-2(S)-hydroxy-propyl(cyclohexylmethyl)phosphinic acid or a salt thereof, can be prepared as follows:

| Composition (for 1000 film-coated tablets) | |
|---|---|
| active ingredient | 400.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed and moistened with a paste, prepared from 15 g of corn starch and water (with heating), and granulated. The granules are dried, the remainder of the corn starch, the talc and the calcium stearate are added and mixed with the granules. The mixture is compressed to form tablets (weight 583 mg) which are coated with a solution of the hydroxypropylmethylcellulose and the shellac in methylene chloride; final weight of the film-coated tablet: 585 mg.

EXAMPLE 16

Hard gelatin capsules, each comprising 500 mg of active ingredient, for example 3-{N-[1-(3-cyanophenyl)ethyl]amino}-2(S)-hydroxy-propyl(cyclohexylmethyl)phosphinic acid or a salt thereof, can be prepared, for example, as follows:

| Composition (for 1000 capsules) | |
|---|---|
| active ingredient | 500.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve having a mesh size of 0.2 mm. The two components are intimately mixed. Then first the lactose is added through a sieve having a mesh size of 0.6 mm and then the microcrystalline cellulose is added through a sieve having a mesh size of 0.9 mm. The components are then intimately mixed again for 10 minutes. Finally, the magnesium stearate is added through a sieve having a mesh size of 0.8 mm. After mixing for a further 3 minutes, 790 mg portions of the resulting formulation are introduced into each of a number of hard gelatin capsules of an appropriate size.

EXAMPLE 17

A 5% injection or infusion solution of 3-{N-[1-(3-cyanophenyl)ethyl]amino}-2(S)-hydroxy-propyl(cyclohexylmethyl)phosphinic acid or a salt thereof can be prepared, for example, in the following manner:

| Composition (for 1000 or 400 ampoules) | |
|---|---|
| active ingredient | 125.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and filtered through a microfilter. The buffer solution is added and the batch is made up to 2500 ml with water. In order to prepare unit dose forms, 1.0 or 2.5 ml portions are introduced into glass ampoules which then contain 50 or 125 mg of active ingredient, respectively.

EXAMPLE 18

In a manner analogous to that described in the above formulation examples, it is also possible to prepare pharmaceutical compositions comprising a different compound of formula I according to any one of Examples 1 to 13.

What is claimed is:

1. A N-aralkyl-aminoalkanephosphinic acid of formula I

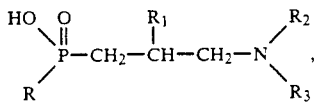

wherein R is an aliphatic, cycloaliphatic, cycloaliphatic-aliphatic or radical having at least 2 carbon atoms, $R_1$ is hydrogen or hydroxy, $R_2$ is an araliphatic or radical substituted by free or functionally modified carboxy that is bonded directly or by way of a spacer, and $R_3$ is hydrogen, lower alkyl or a group $R_2$, or a salt thereof.

2. A N-aralkyl-aminoalkanephosphinic acid of formula I

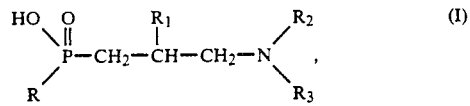

wherein R is lower alkyl having at least 2 carbon atoms, lower alkenyl, lower alkynyl, oxo-lower alkyl, hydroxy- or dihydroxy-lower alkyl, hydroxy-lower alkenyl, mono-, di- or poly-halo-lower alkyl, mono-, di- or poly-halo-lower alkenyl, mono-, di- or poly-halo(hydroxy)-lower alkyl, mono-, di- or poly-halo(hydroxy)-lower alkenyl, lower alkoxy-lower alkyl, di-lower alkoxy-lower alkyl, lower alkoxy(hydroxy)-lower alkyl, lower alkoxy(halo)-lower alkyl, lower alkylthio-lower alkyl, di-lower alkylthio-lower alkyl, cycloalkyl, hydroxycycloalkyl, oxa-, dioxa-, thia- and dithia-cycloalkyl, cycloalkyl-lower alkyl, cycloalkenyl-lower alkyl, cycloalkyl(hydroxy)-lower alkyl, (lower alkyl thio)cycloalkyl(hydroxy)-lower alkyl, or mono- or di-phenyl-lower alkyl that is unsubstituted or mono-, di- or tri-substituted by lower alkyl, lower alkoxy, halogen, hydroxy and/or by trifluoromethyl, naphthyl-lower alkyl, $R_1$ is hydrogen or hydroxy, $R_2$ is a phenyl-lower alkyl radical that is mono- or di-substituted by carboxy; lower alkoxycarbonyl; cyano; carbmoyl; N-mono- or N,N-di-lower alkylcarbamoyl; carboxy-lower alkyl; lower alkoxycarbonyl-lower alkyl; cyano-lower alkyl; carbamoyl-lower alkyl; N-mono- or N,N-di-lower alkylcarbamoyl-lower alkyl; and $R_3$ is hydrogen, lower alkyl or $R_2$, or a salt thereof.

3. A compound according to claim 2 of formula I, wherein R is $C_3$–$C_7$alkyl, $\alpha,\alpha$-di-$C_1$-$C_4$-alkoxy-$C_1$-$C_4$alkyl, $C_3$-$C_6$cycloalkyl-$C_1$-$C_4$alkyl, $C_3$-$C_6$cycloalkenyl-$C_1$-$C_4$alkyl, or is phenyl-$C_1$-$C_4$alkyl that is unsubstituted or mono-, di- or tri-substituted by $C_1$-$C_4$alkyl, $C_1$-$C_4$alkoxy, hydroxy and/or by halogen, $R_1$ is hydrogen or hydroxy, $R_2$ is a phenyl-, radical that is mono- or di-substituted by carboxy; $C_1$-$C_4$alkoxycarbonyl; cyano; carbamoyl; N-mono- or N,N-di-$C_1$-$C_4$alkylcarbamoyl; carboxy-$C_1$-$C_4$alkyl; $C_1$-$C_4$alkoxycarbonyl-$C_1$-$C_4$alkyl; cyano-$C_1$-$C_4$alkyl; carbamoyl$C_1$-$C_4$alkyl; N-mono- or N,N-di-$C_1$-$C_4$alkylcarbamoyl-$C_1$-$C_4$alkyl; and $R_3$ is hydrogen or $C_1$-$C_4$alkyl, or a salt thereof.

4. A compound according to claim 2 of formula I, wherein R is $C_3$-$C_5$alkyl, $\alpha,\alpha$-di-$C_1$-$C_4$alkoxymethyl, $C_3$-$C_6$cycloalkyl-$C_1$-$C_4$alkyl or benzyl, $R_1$ is hydrogen or hydroxy, $R_2$ is an $\alpha$-phenyl-$C_1$-$C_4$alkyl which radical is mono- or di-substituted by carboxy, $C_1$-$C_4$alkoxycarbonyl, cyano, carbamoyl, carboxy-$C_1$-$C_4$alkyl, $C_1$-$C_4$alkoxycarbonyl-$C_1$-$C_4$alkyl, cyano-$C_1$-$C_4$alkyl, carbamoyl-$C_1$-$C_4$alkyl, and each of which radicals $\alpha$-phenyl-$C_1$-$C_4$alkyl may be additionally substituted by $C_1$-$C_4$alkoxy, trifluoromethoxy, halogen or by trifluoromethyl, and $R_3$ is hydrogen, or a salt thereof.

5. A compound according to claim 2 of formula I, wherein R is $\alpha,\alpha$-di-$C_1$-$C_4$alkoxymethyl, $C_3$-$C_6$cycloalkyl-$C_1$-$C_4$alkyl, $C_3$-$C_6$cycloalk-3-enyl-$C_1$-$C_4$alkyl or benzyl, $R_1$ is hydroxy, $R_2$ is a phenyl-$C_1$-$C_4$alkyl radical that is substituted by carboxy, cyano, and $R_3$ is hydrogen, or a pharmaceutically acceptable salt thereof.

6. A compound according to claim 2 of formula I in which the carbon atom of the propylene chain that is bonded to the group $R_1$, if $R_1$ is hydroxy, and/or a chiral α-carbon atom of the aliphatic moiety of the radical $R_2$, if present, each have the (S) configuration.

7. A compound according to claim 2 being 3-{N-[1(R)-(3-carboxyphenyl)ethyl]amino}-2(S)-hydroxy-propyl(cyclohex-3-enylmethyl)phosphinic acid or a pharmaceutically acceptable salt thereof.

8. A compound according to claim 2 being 3-{N-[1(S)-(4-carboxyphenyl)ethyl]amino}-2(S)-hydroxy-propyl(cyclohex-3-enylmethyl)phosphinic acid or a pharmaceutically acceptable salt thereof.

9. A compound according to claim 2 being 3-{N-[1-(4-cyanophenyl)ethyl]amino}-2(S)-hydroxy-propyl(-benzyl)phosphinic acid or a pharmaceutically acceptable salt thereof.

10. A compound according to claim 2 being 3-{N-[1-(3-cyanophenyl)ethyl]amino}-2(S)-hydroxy-propyl(-benzyl)phosphinic acid or a pharmaceutically acceptable salt thereof.

11. A compound according to claim 2 being 3-{N-[1-(4-carboxyphenyl)ethyl]amino}-2(S)-hydroxy-propyl(-benzyl)phosphinic acid or a pharmaceutically acceptable salt thereof.

12. A compound according to claim 2 being 3-{N-[1-(4-carboxyphenyl)ethyl]amino}-2(S)-hydroxy-propyl(-benzyl)phosphinic acid or a pharmaceutically acceptable salt thereof.

13. A compound according to claim 2 being 3-{N-[1-(3-carboxyphenyl)ethyl]amino}-2(S)-hydroxy-propyl(-benzyl)phosphinic acid or a pharmaceutically acceptable salt thereof.

14. A compound according to claim 2 being 3-{N-[1-(3-carboxy-4-methoxyphenyl)ethyl]amino}-2(S)-hydroxy-propyl(benzyl)phosphinic acid or a pharmaceutically acceptable salt thereof.

15. A compound according to claim 2, said compound being
3-{N-[1-(4-carboxymethylphenyl)ethyl]amino}-2(S)-hydroxy-propyl(cyclohexylmethyl)phosphinic acid; or a pharmaceutically acceptable salt thereof.

16. A compound according to claim 2 selected from the group consisting of
3-{N-[1-(R)-(3-carboxyphenyl)ethyl]amino}-2-(S)-hydroxy-propyl(diethoxymethyl)phosphinic acid;
3-{N-[1-(S)-(3-carboxyphenyl)ethyl]amino}-2-(S)-hydroxy-propyl(diethoxymethyl)phosphinic acid.

17. A pharmaceutical composition comprising a compound according to claim 1 in free form or in the form of a pharmaceutically acceptable salt, together with customary pharmaceutical excipients.

18. A method of treatment of epilepsies and/or cerebral insufficiencies characterized in that a therapeutically effective amount of a compound according to claim 1 or a pharmaceutically acceptable salt thereof is administered to a warm-blooded organism in need of such treatment.

19. A compound according to claim 1, said compound selected from the group consisting of
3-{N-[1-(3-cyanophenyl)ethyl]amino}-2(S)-hydroxy-propyl(cyclohexylmethyl)phosphinic acid;
3-{N-[1-(3-carboxyphenyl)ethyl]amino}-2(S)-hydroxy-propyl(cyclohexylmethyl)phosphinic acid;
3-{N-[1-(4-cyanophenyl)ethyl]amino}-2(S)-hydroxy-propyl(cyclohexylmethyl)phosphinic acid;
3-{N-[1(S)-(4-cyanophenyl)ethyl]amino}-2(S)-hydroxy-propyl(cyclohexylmethyl)phosphinic acid;
3-{N-[1(R)-(4-cyanophenyl)ethyl]amino}-2(S)-hydroxy-propyl(cyclohexylmethyl)phosphinic acid;
3-{N-[1(S)-(3-cyanophenyl)ethyl]amino}-2(S)-hydroxy-propyl(cyclohexylmethyl)phosphinic acid;
3-{N-[1(S)-(3-cyanophenyl)ethyl]amino}-2(R)-hydroxy-propyl(cyclohexylmethyl)phosphinic acid;
3-{N-[1(R)-(3-cyanophenyl)ethyl]amino}-2(S)-hydroxy-propyl(cyclohexylmethyl)phosphinic acid;
3-{N-[1-(4-carboxyphenyl)ethyl]amino}-2(S)-hydroxy-propyl(cyclohexylmethyl)phosphinic acid;
3-{N-[1(S)-(4-carboxyphenyl)ethyl]amino}-2(S)-hydroxy-propyl(cyclohexylmethyl)phosphinic acid;
3-{N-[1(R)-(4-carboxyphenyl)ethyl]amino}-2(S)-hydroxy-propyl(cyclohexylmethyl)phosphinic acid;
3-{N-[1(S)-(3-carboxyphenyl)ethyl]amino}-2(S)-hydroxy-propyl(cyclohexylmethyl)phosphinic acid;
3-{N-[1(S)-(3-carboxyphenyl)ethyl]amino}-2(R)-hydroxy-propyl(cyclohexylmethyl)phosphinic acid; and
3-{N-[1(R)-(3-carboxyphenyl)ethyl]amino}-2(S)-hydroxy-propyl(cyclohexylmethyl)phosphinic acid;
or a pharmaceutically acceptable salt thereof.

* * * * *